(12) United States Patent
Parimoo et al.

(10) Patent No.: US 9,044,408 B2
(45) Date of Patent: Jun. 2, 2015

(54) COSMETIC USE OF N-HETEROARYLBISAMIDE ANALOGS AND RELATED COMPOUNDS

(75) Inventors: Satish Parimoo, Bridgewater, NJ (US);
Nancy T. Ilaya, New York, NY (US);
John W. Lyga, Basking Ridge, NJ (US)

(73) Assignee: Avon Products, Inc., New York, NY (US)

( * ) Notice: Subject to any disclaimer, the term of this patent is extended or adjusted under 35 U.S.C. 154(b) by 205 days.

(21) Appl. No.: 13/285,458

(22) Filed: Oct. 31, 2011

(65) Prior Publication Data

US 2013/0109691 A1    May 2, 2013

(51) Int. Cl.
| | | |
|---|---|---|
| *A61K 31/415* | (2006.01) | |
| *A61Q 19/08* | (2006.01) | |
| *A61P 17/02* | (2006.01) | |
| *A61K 8/49* | (2006.01) | |

(52) U.S. Cl.
CPC ............... *A61K 8/494* (2013.01); *A61Q 19/08* (2013.01); *A61K 31/415* (2013.01)

(58) Field of Classification Search
None
See application file for complete search history.

(56) References Cited

U.S. PATENT DOCUMENTS

| | | | |
|---|---|---|---|
| 3,632,783 A | | 1/1972 | Stonis |
| 6,849,658 B2 * | | 2/2005 | Bernardon et al. ........... 514/432 |
| 7,622,448 B2 * | | 11/2009 | Dalko et al. .................... 514/23 |
| 7,625,914 B2 * | | 12/2009 | Clary et al. .................... 514/275 |
| 7,629,375 B2 * | | 12/2009 | Wang et al. .................... 514/407 |
| 2007/0065443 A1 | | 3/2007 | Tobia et al. |
| 2008/0207725 A1 | | 8/2008 | Barker et al. |
| 2010/0273797 A1 | | 10/2010 | Boman et al. |

OTHER PUBLICATIONS

"Side Reactions in Organic Synthesis" by Dorwald, Wiley (Germany), p. IX (2005).*
Fisher GJ, Kang S, Varani J, Bata-Csorgo Z, Wan Y, Datta S, Voorhees JJ (2002). Mechanisms of photoaging and chronological skin aging. Arch Dermatol 138: 1462-1470.
Nichols JA, Katiyar SK (2010), Skin photoprotection by natural polyphenols: anti-inflammatory, antioxidant and DNA repair mechanisms. Arch Dermatol Res 302: 71-83.
Kuilman T, Peeper DS (2009). Senescence-messaging secretome: SMS-ing cellular stress. Nature reviews Cancer 9: 81-94.
Heng MC (2010). Curcumin targeted signaling pathways: basis for anti-photoaging and anti-carcinogenic therapy. Int J Dermatol 2010. 49: 608-622.
Camougrand, N. and M. Rigoulet (2001). Aging and oxidative stress: studies of some genes involved both in aging and in response to oxidative stress. Respir Physiol 128: 393-401.

* cited by examiner

*Primary Examiner* — Theodore R West
(74) *Attorney, Agent, or Firm* — David M. Joyal; Joan M. McGillycuddy (57) ABSTRACT

Cosmetic and dermatological compositions comprising N-heteroarylbisamide analogs and methods of using such compositions to impart anti-aging benefits to the skin and/or improve skin conditions resulting from reduced collagen and hyaluronic acid production are disclosed. The N-heteroarylbisamides are believed to stimulate collagen and hyaluronic acid production and restore or maintain homeostasis for these compounds.

21 Claims, 3 Drawing Sheets

Hematoxylin and Eosin Stained Vehicle Control (Day 9)

FIG. 1A

Hematoxylin and Eosin Stained Analog A Treated (Day 9)

FIG. 1B

HABP Stained Vehicle Treated (Day 9)

FIG. 2A

HABP Stained Analog A Treated (Day 9)

FIG. 2B

Procollagen 1 Stained Vehicle Treated (Day 9)

FIG. 3A

Procollagen 1 stained Analog A Treated (Day 9)

FIG. 3B

COSMETIC USE OF N-HETEROARYLBISAMIDE ANALOGS AND RELATED COMPOUNDS

FIELD OF INVENTION

The present invention relates generally to compositions for topical application to the skin which comprise N-heteroarylbisamide analogs and the use of such compositions to improve the condition and aesthetic appearance of the skin.

BACKGROUND OF THE INVENTION

Collagen is the body's major structural protein and is composed of three protein chains wound together in a tight triple helix. This unique structure gives collagen a greater tensile strength than steel. Approximately 33 percent of the protein in the body is collagen. Collagen, which occurs in several different forms, plays a key role in providing the structural scaffolding surrounding cells that helps to support cell shape and differentiation, similar to how steel rods reinforce a concrete block. Collagen 1, which is the most prevalent form, provides the supportive framework for the skin.

Collagen is secreted by fibroblasts, which are specialized skin cells located in the dermis. In order to signal or turn on the production of skin structural proteins, fibroblast cells have specially shaped receptors on their outside membranes that act as binding sites to which signal molecules with a matching shape can fit. When the receptors are bound by the correct combination of signal molecules (called fibroblast growth factors, or FGFs), the fibroblast begins the production of collagen. This occurs initially through the production of procollagen, a water soluble pre-eursor, within the fibroblast cells and subsequently through the assembly of procollagen threads into insoluble collagen fibers within the extracellular matrix.

Fibroblasts also produce other skin structural proteins such as elastin (a protein which gives the skin its ability to snap back) and glucosaminoglycans (GAGs). GAGs make up the ground substance that keeps the dermis hydrated. Hyaluronic acid is an example of a GAG. Hyaluronic acid is a polysaccharide that is responsible for lubricating and moisturizing many of the body's cells. Over 50% of the body's hyaluronic acid is present within the skin. Hyaluronic acid can bind up to 1000 times its weight in water and thus keeps moisture within skin's extracellular matrix, the fluid-filled space between cells, maintaining the youthful appearance of skin.

Collagen and GAGs, such as hyaluronic acid, work in concert to give skin its strength, durability, and smooth, plump appearance. The body's ability to regenerate collagen and hyaluronic acid is affected over time by intrinsic and extrinsic factors that include normal aging, disease, and environmental factors. The most common causes of this are UV radiation (photoaged skin) and age (chronologically aged skin) although factors such as smoking, poor nutrition, chronic stress, certain medications (non-steroidal anti-inflammatory drugs, hormonal treatments, chemotherapy, etc.), and diseases, particularly autoimmune conditions that target collagen, also impair the body's ability to produce and maintain the necessary levels of collagen and hyaluronic acid.

The common phenotypic signs of photoaged skin include wrinkles, roughness, mottled pigmentation, changes in epidermal thickness, skin sagging and reduced ability to regenerate. A number of growth factors and cytokines, such as EGF, IL1 and TNF-α, are induced in skin cells as a result of UV damage. These UV induced factors trigger a signal transduction cascade that ultimately leads to an increase in expression of transcription factor AP-1. The result of the enhanced expression and activity of AP-1 is increased expression of matrix metalloproteinases (MMPs), decreased procollagen synthesis and biochemical changes in extracellular matrix and epidermis that progress with age and define the aged-skin phenotype. Fisher G J, Kang S, Varani J, Bata-Csorgo Z, Wan Y, Datta S, Voorhees J J (2002). Mechanisms of photoaging and chronological skin aging. *Arch Dermatol* 138: 1462-1470. Expression of proinflammatory genes and molecules, such as COX-2 and prostaglandin, have also been found to result from UV-B radiation exposure, Nichols J A, Katiyar S K (2010), Skin photoprotection by natural polyphenols: anti-inflammatory, antioxidant and DNA repair mechanisms. *Arch Dermatol Res* 302: 71-83, and are associated with cellular senescence Kuilman T, Peeper D S (2009). Senescence-messaging secretome: SMS-ing cellular stress. *Nature reviews Cancer* 9: 81-94, and Heng M C (2010). Curcumin targeted signaling pathways: basis for anti-photoaging and anti-carcinogenic therapy. *Int J Dermatol* 2010. 49: 608-622. Hence controlling inflammation in photo aging is of interest for skin anti-aging regimen.

In contrast to UV induced photo aging, chronological aging of the skin is a natural process that occurs gradually over the lifetime of an individual. Photo protected aged skin, which develops less mottled pigmentation with finer lines, is generally thinner and more lax than photo-aged skin, Accumulation of molecular damage (including DNA) caused by an increase in reactive oxygen species (ROS) is common to both photo- and non-photo skin aging process. Like photo aging chronological aging is thought to strongly involve the accumulation of damage caused by an increase ROS induced by mitochondrial oxidative metabolism, Camougrand, N. and M. Rigoulet (2001), Aging and oxidative stress: studies of some genes involved both in aging and in response to oxidative stress. *Respir Physiol* 128: 393-401.

The stimulation of collagen and hyaluronic acid production may reverse some of the damage caused by UV rays and the passage of time, and thus the discovery of natural or synthetic compounds that are safe and effective in reversing and or halting the skin aging or photoaging is of great interest to consumers. The present invention thus provides new compositions and methods for stimulating collagen and hyaluronic acid production. It is a further object of the invention to improve the overall appearance of skin, including reversing, and/or preventing signs of aging, such as skin wrinkles, by stimulating collagen and hyaluronic acid production with cosmetic compositions comprising effective amounts of N-heteroarylbisamide analogs. A further object of the invention is to prevent, and or ameliorate various conditions of the skin resulting from disruption of collagen or hyaluronic acid homeostasis, i.e. increased degradation with insufficient production thereof or vice versa, through the administration of a dermatologically effective amount of a N-heteroarylbisamide analog to a subject in need thereof.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that N-heteroarylbisamides are stimulators of collagen and hyaluronic acid production and thus are beneficial agents against various signs of intrinsic aging and photo-aging of skin and conditions of the skin resulting from the disruption of collagen or hyaluronic acid homeostasis.

In one aspect of the invention, cosmetic compositions are provided for improving the aesthetic appearance of skin comprising, in a cosmetically acceptable vehicle, a dermatologically effective amount of an N-heteroarylbisamide having the structure of formula I:

Q is N or C;
R, $R_2$, $R_{2'}$, $R_3$, $R_4$ and $R_6$ are independently H, $C_1$-$C_8$ alkyl, heteroalkyl, alkoxyalkyl, heteroalkoxyalkyl, $C_3$-$C_8$ cycloalkyl, heterocycloalkyl, and, heteroaryl, alkyl-aryl, heteroalkyl-aryl, aryl-alkyl, and/or heteroaryl-alkyl;
$R_1$ and $R_5$ are independently H, alkyl, heteroalkyl, cycloalkyl, heterocycloalkyl, aryl, heteroaryl, arylalkyl, heteroarylalkyl, alkoxyalkyl, or heteroalkoxyalkyl or WR wherein W is CO, $CO_2$, CONH, $SO_2$, $PO_3$, or C(Oalkyl)$_2$.
$R_1$, $R_2$, $R_{2'}$, $R_5$, and $R_6$ each may also be optionally substituted with, for example, halogen, amino, alkoxy, heteroalkoxy, alkyl, heteroalkyl, alkenyl, heteroalkenyl, alkynyl, heteroalkynyl, cycloalkyl, heterocycloalkyl, aryl, heteroaryl, etc.
and n is 1-8.

In another aspect of the invention, a method is provided for improving the aesthetic appearance of human skin comprising topically applying to an area of the skin in need thereof an amount of the cosmetic composition or a cosmetically acceptable salt thereof in a cosmetically acceptable vehicle effective to enhance the skin. The skin enhancements may be in the form of increasing production of procollagen/collagen and/or hyaluronic acid, restoring collagen and/or hyaluronic acid homeostasis within the extracellular matrix, improving the quality and mechanical properties of existing collagen, modulating the activity of fibroblasts and/or keratinocytes, and ultimately, improving and maintaining the quality and viability of the extracellular matrix and epidermis.

Also provided is a method of treating one or more signs of skin aging comprising topically applying to skin in need thereof an N-heteroarylbisamide according to formula I in a dermatologically effective amount.

In another aspect of the invention, a method of improving, ameliorating, and/or preventing fine lines or wrinkles or sagging in human skin is provided, comprising topically applying to skin in need thereof, including applying directly to a wrinkle or fine line, a composition comprising a N-heteroarylbisamide according to formula (In an amount effective to enhance the skin.

In a further aspect of the invention, a method of improving, ameliorating, and/or preventing cosmetic or dermatological manifestations of various diseases such as lesions or inflammation resulting from diabetes or collagen diseases (rheumatoid arthritis, dermatomyositis, etc.) or dermal atrophy such as that which occurs from the chronic use/administration of various therapeutics such as NSAIDS, steroids (cortisone, etc.) or hormonal therapies by administering to an area of skin in need thereof a dermatologically effective amount of a compound of formula I in a dermatologically acceptable vehicle.

These and other aspects of the present invention will be better understood by reference to the following detailed description and accompanying figures.

DETAILED DESCRIPTION

All terms used herein are intended to have their ordinary meaning unless otherwise provided.

As used herein, the term "consisting essentially of" is intended to limit the invention to the specified materials or steps and those that do not materially affect the basic and novel characteristics of the claimed invention, as understood from a reading of this specification. All percentages are by weight based on the total weight of the composition, unless otherwise indicated.

As used herein, the prefix "hetero-" as in "heteroalkyl," "heteroalkenyl," "heteroalkynyl," etc. refers to a residue wherein one or more of the carbons of the backbone residue are replaced with O, S, or N heteroatoms or combinations thereof.

As used herein, the terms "prevent," "preventing," etc. means delaying the onset, hindering the progress, hindering the appearance, protection against, inhibiting or eliminating the emergence, or reducing the incidence, of various cosmetic or dermatologic conditions, damages, effects or symptoms. Use of the term "prevention" is not meant to imply that all subjects in a subject population administered the cosmetic composition will never be affected by or develop the cosmetic or dermatologic conditions, damage, effect or symptom, but rather that the subject population will exhibit a reduction in the cosmetic or dermatologic damages, effects, or symptoms. For example, many flu vaccines are not 100% effective at preventing flu in those administered the vaccine.

As noted above, the common phenotypic signs of aging (chronological or photo) may include, but are not limited to, the appearance of and/or increase in size or number of wrinkles or fine lines including, but not limited to, atrophic crinkling rhytids, permanent elastic creases, dynamic expression lines (frown/laugh lines, crow's feet, etc.) or gravitational folds; increased pore size; dulling of the skin; deterioration of skin texture; impairment of skin barrier repair i.e. increased bruising which takes longer to heal and may result in skin ulcers; and drying of the skin. The phenotype differences between chronological and photo aged skin are largely related to the thickness of the skin and uniformity of pigmentation: chronologically aged skin tends to thin and slacken while maintaining an even pigmentation, whereas photoaged skin tends to be rough with leathery texture while assuming a mottled pigmentation. The underlying damage to the extracellular matrix, the proteins and fibers between the skin cells that provide a scaffolding to support the cells and a means of supplying the cells with nutrients, may largely be responsible for these changes within the skin's appearance. The damage to the extracellular matrix may include, but is not limited to, disruptions in the homeostasis of collagen such as increased degradation without equal production thereof, reduction in the quality of the collagen and mechanical properties thereof; disruptions in the homeostasis of hyaluronic acid; the presence of scars and/or the increase in number or size thereof; and die over production or accumulation of inflammatory transcription factors, such as AP-1, or cytokines such as MMP. Further, although the disruption of the extracellular matrix may largely be responsible for aging phenotypes the epidermis is also affected by the process of aging resulting in a thinning of the epidermis in chronological aging and the presence of atypia (cells of varying sizes and shapes) within the epidermis of photoaged skin. Additional, conditions of the skin such as, scarring, oily, dry or combination skin-type, increased pore sizes and/or uneven pigmentation may also be a result of the above-noted changes within the extracellular matrix and epidermis.

The present invention provides compositions for topical application which comprise an effective amount of N-heteroarylbisamides or a related compound that improve, reverse, ameliorate and/or prevent signs of skin aging. The compositions of the current invention may accomplish this by enhancing the skin, i.e., improving the condition, structure, quality, viability or production of a skin component. Various skin enhancements may include, but are not limited to, increasing production of procollagen/collagen and/or hyaluronic acid, restoring collagen and/or hyaluronic acid homeostasis within the extracellular matrix, improving the quality and mechanical properties of existing collagen, modulating the activity of fibroblasts and/or keratinocytes, and ultimately, improving and maintaining the quality and viability of the extracellular matrix and epidermis. The increase of collagen (amount, quality and/or mechanical properties thereof) within the extracellular matrix may lead to aesthetic improvements including but not limited to, the treatment, reduction, and/or prevention of the appearance of fine lines or wrinkles, improvement in the skin's thickness, plumpness, and/or tautness; improvement in skin barrier repair and/or function; improvement in appearance of skin contours; increased skin elasticity and/or resiliency; treatment, reduction, and/or prevention of skin sagging; smoothing scars and stretch marks; and/or reduction of pore size. The increase in hyaluronic acid may lead to aesthetic improvements including but not limited to, improvement in the skin's suppleness, softness, tone, radiance, and/or clarity; improvement in the skin texture and/or promotion of its retexturization; restoration of skin luster and/or brightness; replenishment of essential nutrients and/or constituents in the skin; and/or improvement in skin moisturization and/or type. The modulation of fibroblasts may lead to an increase in collagen and hyaluronic acid, and the concomitant benefits thereof noted above, increase in the production of other structural proteins and glucosaminoglycans; improvements in the structure of collagen; homoeostasis of structural protein and glucosaminoglycans; down regulation of cytokine production; increased activation of fibroblasts to fibrocytes; increases in the viability and/or function of fibroblasts; improvement in maintenance and remodeling of elastin; and/or improvement in skin barrier repair and/or function. The modulation of keratinocytes may improve the viability and/or function of the keratinocytes; and/or down regulate the production of inflammatory factors and/or cytokines; and may lead to aesthetic improvements including but not limited to, improvement in skin barrier repair and/or function; improvement of thickness of the epidermis; improvement in uniformity of epidermal cells; and/or smoothing scars and stretch marks. Improving and maintaining the quality and viability of the extracellular matrix may result in aesthetic improvements including, but not limited to, the treatment, reduction, and/or prevention of the appearance of fine lines or wrinkles, improvement in the skin's thickness, plumpness, and/or tautness; improvement in skin barrier repair and/or function; improvement in appearance of skin contours; increased skin elasticity and/or resiliency; treatment, reduction, and/or prevention of skin sagging; smoothing scars and stretch marks; reduction of pore size; improvement in the skin's suppleness, softness, tone, radiance, and/or clarity; improvement in the skin texture and/or promotion of its retexturization; restoration of skin luster and/or brightness; replenishment of essential nutrients and/or constituents in the skin; and/or improvement in skin moisturization and/or type. Improvements in the function and/or viability of the epidermis may result in aesthetic improvements including, but not limited to, improvement in skin barrier repair and/or function; improvement of thickness of the epidermis; improvement in uniformity of epidermal cells; improvement in pigmentation; and/or smoothing scars and stretch marks.

In practice, the compositions of the invention are applied to skin in need of treatment. That is, skin which suffers from one or more of the following aesthetic issues: chronological aging, photoaging, actinic aging, scars, wrinkles, lack of luster, dryness, oiliness, mixed complexion, lesions or difficulty healing, thinness, hardness, inelasticity, lack of tone, poor texture, large pores, uneven pigmentation, sagging, and/or similar conditions of the skin or which would otherwise benefit from aesthetic improvement.

In certain preferred embodiments the compositions and methods of the invention are directed to the prevention and/or amelioration of fine lines and/or wrinkles in the skin. In this case, the compositions are applied to skin in need thereof, by which is meant skin having wrinkles and/or fine lines. Preferably, the compositions are applied directly to the fine lines and/or wrinkles. The compositions and methods are suitable for ameliorating fine lines and/or wrinkles on any surface of the skin, including without limitation, the skin of the face, neck, and/or hands.

The cosmetic compositions for treating a skin condition associated with loss of collagen and/or hyaluronic acid comprise, in a cosmetically acceptable vehicle, an amount of an N-heteroarylbisamide analog effective to achieve aesthetic improvements. These agents may have the structure of formula (I):

(I)

In formula (I), Q is N or C; R, $R_2$, $R_{2'}$, $R_3$, $R_4$ and $R_6$ are independently H, alkyl, heteroalkyl, cycloalkyl, heterocycloalkyl, aryl, heteroaryl, arylalkyl, heteroarylalkyl, alkoxyalkyl, or heteroalkoxyalkyl; $R_1$ and $R_5$ are independently H, alkyl, heteroalkyl, cycloalkyl, heterocycloalkyl, aryl, heteroaryl, arylalkyl, heteroarylalkyl, alkoxyalkyl, or heteroalkoxyalkyl or WR wherein W is CO, $CO_2$, CONH, $SO_2$, $PO_3$, or $CH(Oalkyl)_2$; and n is 1-8.

In one embodiment, $R_1$, $R_3$, $R_4$ and $R_5$ independently represent lower alkyl group (e.g., methyl, ethyl, propyl, butyl, etc.), and typically are methyl or ethyl. In another embodiment, $R_1$, $R_3$, $R_4$ and $R_5$ are H. In a further embodiment, R and $R_6$ are independently a $C_1$-$C_8$ alkyl, preferably $C_1$-$C_4$ alkyl, $C_3$-$C_8$ substituted or unsubstituted cycloalkyl, or aromatic hydrocarbon radicals, preferably C6 aromatic hydrocarbon radicals, as exemplified by substituted or unsubstituted aryl (e.g., phenyl), alkyl-aryl (e.g., benzyl), aryl-alkyl, and the like. In other embodiments $R_2$ and $R_{2'}$ represent H, a lower alkyl group (e.g., methyl, ethyl, propyl, butyl, etc.), typically methyl or butyl), or a $C_6$ aromatic hydrocarbon radical substituted or unsubstituted aryl (e.g. phenyl).

R, $R_1$, $R_2$, $R_{2'}$, $R_3$, $R_4$, $R_5$, and $R_6$ each may also be optionally substituted with, for example, halogen, amino, alkoxy, heteroalkoxy, alkyl, heteroalkyl, alkenyl, heteroalkenyl, alkynyl, heteroalkynyl, cycloalkyl, heterocycloalkyl, aryl, heteroaryl, etc.

In a further embodiment, adjacent substituents $R_2$ and $R_{2'}$ and/or $R_3$ and $R_4$, and/or germinal substituents $R_5$ and $R_6$ each taken together can form a 5, 6, or 7 substituted or unsubstituted member ring.

In some embodiments, Q is N. In further embodiments, n is 1-6, and preferably about 1-4.

In one embodiment according to formula (I), R is phenyl, as shown in formula (IA).

(IA)

where $R_2$, $R_{2'}$, $R_6$, and $R_7$ are Independently H, alkyl, heteroalkyl, cycloalkyl, heterocycloalkyl, aryl, heteroaryl, arylalkyl, heteroarylalkyl, alkoxyalkyl, or heteroalkoxyalkyl; $R_1$ and $R_5$ are independently H, alkyl, heteroalkyl, cycloalkyl, heterocycloalkyl, aryl, heteroaryl, arylalkyl, heteroarylalkyl, alkoxyalkyl, or heteroalkoxyalkyl or WR wherein W is CO, $CO_2$, CONH, $SO_2$, $PO_3$, or $CH(Oalkyl)_2$; and n is 1-4.

$R_1$, $R_2$, $R_{2'}$, $R_5$, and $R_6$ each may also be optionally substituted with, for example, halogen, amino, alkoxy, heteroalkoxy, alkyl, heteroalkyl, alkenyl, heteroalkenyl, alkynyl, heteroalkynyl, cycloalkyl, heterocycloalkyl, aryl, heteroaryl, etc.

In a further embodiment, adjacent substituents $R_2$ and $R_{2'}$ and/or geminal substituents $R_5$ and $R_6$ each taken together can form a 5, 6, or 7 substituted or unsubstituted member ring.

In a further embodiment, $R_7$ is H, halogen, or $C_1$-$C_4$ alkyl or alkoxy; $R_2$ is $C_1$-$C_6$ alkyl, or an $C_6$ aromatic hydrocarbon radical; $R_{2'}$ is H or an $C_6$ aromatic hydrocarbon radical; $R_1$ and $R_5$ independently represent lower alkyl group (e.g., methyl, ethyl, propyl, butyl, etc.), typically methyl or ethyl; and $R_6$ is a $C_1$-$C_5$ alkyl group, substituted or unsubstituted $C_3$-$C_6$ cycloalkane, or substituted or unsubstituted aromatic hydrocarbon radical; and n is 2-3.

In yet a further embodiment, $R_7$ is chlorine or methyl; $R_2$ is methyl or tert-butyl; $R_{2'}$ is H or phenyl; $R_1$ and $R_5$ are H; and $R_6$ is propyl, substituted propyl, or substituted phenyl; and n is 3.

A non-limiting list of compounds within the scope of formula (IA) is noted in Table 1 below.

TABLE 1

FORMULA IA COMPOUNDS

| Analog | $R_1$ | $R_2$ | $R_{2'}$ | $R_5$ | $R_6$ | $R_7$ | n |
|---|---|---|---|---|---|---|---|
| A | H | t-butyl | H | H | 2,3-dimethylpropyl | 3-methyl | 3 |
| B | H | methyl | phenyl | H | propyl | 3,4-dichloro | 3 |
| C | H | t-butyl | H | H | 3,4-dimethylphenyl | 4-methyl | 3 |
| D | H | t-butyl | H | H | 3,4-dimethylphenyl | H | 3 |
| E | H | t-butyl | H | H | 3,4-dimethylphenyl | 4-methyl | 3 |
| F | H | t-butyl | H | H | 3-methylbutyl | 4-methoxy | 3 |
| G | H | t-butyl | H | H | 3-methylbutyl | 3-Cl | 3 |
| H | H | phenyl | H | H | 2-methylethyl | 3-Cl | 3 |
| I | H | phenyl | H | H | 3-morpholinoethyl | 3-Cl | 3 |
| J | H | t-butyl | H | H | propyl | 3-methyl | 2 |
| K | H | t-butyl | H | H | 2,3-dimethylpropyl | 3,4-Cl | 2 |
| L | H | t-butyl | H | H | benzyl | 4-methyl | 2 |
| M | H | t-butyl | H | H | sec-butyl | 4-methoxy | 2 |
| N | H | t-butyl | H | H | methy-2-furanyl | 4-methyl | 2 |
| O | H | methyl | phenyl | H | 3-methylbutyl | 3-Cl | 2 |
| P | H | methyl | phenyl | H | 2-phenylethyl | 3-methyl | 2 |
| Q | H | t-butyl | H | H | benzyl | 3-Cl | 2 |
| R | H | phenyl | H | H | isobutyl | 3-methyl | 2 |
| S | H | phenyl | H | H | cyclohexyl | 3-methyl | 2 |

In a particular embodiment, a cosmetic composition comprises, in a cosmetically acceptable vehicle, preferably a water-in-oil or oil-in-water emulsion, from about 0.0001% to about 90% by weight of a N-heteroarylbisamine analog (Analog A) having the structure:

or a cosmetically acceptable salt thereof.

In another particular embodiment, a cosmetic composition comprises, in a cosmetically acceptable vehicle, preferably a water-in-oil or oil-in-water emulsion, from about 0.0001% to about 90% by weight of a N-heteroarylbisamine analog (Analog B) having the structure:

or a cosmetically acceptable salt thereof.

In another particular embodiment, a cosmetic composition comprises, in a cosmetically acceptable vehicle, preferably a water-in-oil or oil-in-water emulsion, from about 0.0001% to about 90% by weight of a N-heteroarylbisamine analog (Analog C) having the structure:

or a cosmetically acceptable salt thereof.

The invention embraces the use of cosmetically acceptable (e.g., non-toxic and/or non-irritating) salts. Examples of the salts of the compounds in the present invention include salts with alkali metals such as sodium and potassium; salts with alkaline-earth metals such as calcium and magnesium; salts with amines such as monoethanolamine; salts with inorganic acids such as hydrochloric acid and sulfuric acid; and salts with organic acids such as citric acid and acetic acid. Special mention may be made of hydrochloride salts.

The cosmetic compositions according to the invention can be formulated in a variety of forms for topical application and will comprise from about 0.00001% to about 90% by weight of one or more compounds according to formula (I), and preferably will comprise from about 0.001% to about 25% by weight, and more preferably from about 0.001% to about 1% by weight. The compositions will comprise a dermatologically effective amount of the N-heteroarylbisamide analogs according to formula (I), by which is meant an amount sufficient to enhance the aesthetic appearance of a given area of skin when topically applied thereto.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and hexadecane; silicone oils such as cyclomethicone, dimethicone, dimethicone cross-polymer, polysiloxanes and their derivatives, preferably organomodified derivatives; hydrocarbon oils such as mineral oil, petrolatum, isoeicosane and polyisobutene; polyols such as propylene glycol, glycerin, butylene glycol, pentylene glycol and hexylene glycol; waxes such as beeswax and botanical waxes; or any combinations or mixtures of the foregoing.

The vehicle may comprise an aqueous phase, an oil phase, an alcohol, a silicone phase or mixtures thereof. The cosmetically acceptable vehicle may also comprise an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions. The emulsion may include an emulsifier, such as a nonionic, anionic or amphoteric surfactant.

The oil phase of the emulsion preferably has one or more organic compounds, including emollients; humectants (such as propylene glycol and glycerin); other water-dispersible or water-soluble components including thickeners such as veegum or hydroxyalkyl cellulose; gelling agents, such as high MW polyacrylic acid, i.e. CARBOPOL 934; and mixtures thereof. The emulsion may have one or more emulsifiers capable of emulsifying the various components present in the composition.

The compounds suitable for use in the oil phase include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

The oil phase may comprise one or more waxes, including for example, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Non-limiting emulsifiers included emulsifying waxes, emulsifying polyhydric alcohols, polyether polyols, polyethers, mono- or di-ester of polyols, ethylene glycol mono-stearates, glycerin mono-stearates, glycerin di-stearates, silicone-containing emulsifiers, soya sterols, fatty alcohols such as cetyl alcohol, fatty acids such as stearic acid, fatty acid salts, and mixtures thereof. The preferred emulsifiers include soya sterol, cetyl alcohol, stearic acid, emulsifying wax, and mixtures thereof. Other specific emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, die disclosure of which is hereby incorporated by reference.

These emulsifiers typically will be present in the composition in an amount from about 0.001% to about 10% by weight, in particular. In an amount from about 0.01% to about 5% by weight, and more preferably, below 1% by weight.

The oil phase may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicone materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

The water-in-silicone emulsion may be emulsified with a nonionic surfactant (emulsifier) such as, for example, polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -$(EO)_m$— and/or —$(PO)_n$— groups, where EO is ethyleneoxy and PO is 1,2-propyleneoxy, the side chains being typically capped or terminated with hydrogen or lower alkyl groups (e.g., $C_{1-6}$, typically $C_{1-3}$). Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWET series of emulsifiers sold by OSI Specialties (Danbury, Conn.).

Examples of water-in-silicone emulsifiers include, but are not limited to, dimethicone PEG 10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane. Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

The water-in-silicone emulsifiers typically will be present in the composition in an amount from about 0.001% to about 10% by weight, in particular in an amount from about 0.01% to about 5% by weight, and more preferably, below 1% by weight.

The aqueous phase of the emulsion may include one or more additional solvents, including lower alcohols, such as ethanol, isopropanol, and the like. The volatile solvent may also be a cosmetically acceptable ester such as butyl acetate or ethyl acetate; or the like.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20%) to about 60% by weight of the total emulsion. The aqueous phase will typically comprise from about 25% to about 100%, more typically from about 50% to about 95%) by weight water.

The compositions may include liposomes. The liposomes may comprise other additives or substances and/or may be modified to more specifically reach or remain at a site following administration.

Additionally, the compositions may incorporate encapsulation and/or microencapsulation technology. As is well known in the art, encapsulating materials can be selected which will release the composition upon exposure to moisture, pH change, temperature change, solubility change, or mechanical shear or rupture. Suitable encapsulating materials and methods of preparing encapsulated materials, such as spray drying, extrusion, coacervation, fluidized bed coating, liposome entrapment and others, are disclosed in, for example, U.S. Patent Application Publication No. 2005/0000531 to Shi; Uhlmann, et al, "Flavor encapsulation technologies: an overview including recent developments" Perfumer and Flavorist, 27, 52-61, 2002; and "Selection of Coating and Microencapsulation Processes" by Robert E. Sparks and Irwin Jacobs in Controlled-Release Delivery Systems for Pesticides, Herbert B. Seller ed., Marcel Dekker, New York, N.Y., 1999, pp. 3-29, the contents of which are hereby incorporated by reference.

The compositions incorporating encapsulation and/or microencapsulation technology may form nanoparticles. The term "nanoparticle" as used herein refers to a nanometer-sized particle, having a diameter of between about 1 nanometer and about 999 nanometers; the term "nanoparticles" as used herein refers to nanometer-sized particles, nanoclusters, clusters, particles, small particles, and nanostructured materials.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfoliants, lubricants, fragrances, colorants, depigmenting agents, hypopigmenting agents, preservatives, stabilizers, photostabiling agents, sunscreens, and mixtures thereof. In addition to the foregoing, the cosmetic compositions of the invention may contain any other compound for the treatment of skin disorders. Such additional actives and/or excipients may work in conceit with the compositions of the current invention to achieve cumulative or synergistic improvements in the aesthetic appearance.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol®, polyethylene powder, Teflon®, starch, boron nitride, copolymer microspheres such as Expancel® (Nobel Industries), Polytrap® (Dow Corning) and silicone resin microbeads (Tospearl® from Toshiba), and the like.

In one embodiment of the invention, the compositions may include additional skin actives such as, but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors to achieve cumulative or synergistic improvements in the aesthetic appearance of the treated skin.

In a specific embodiment, the composition may comprise at least one additional botanical, such as, for example, a botanical extract, an essential oil, or the plant itself. Suitable botanicals include, without limitation, extracts from *Abies pindrow*, *Acacia catechu*, *Alisma orientate*, Aloe, *Amorphophallus campanulatus*, *Anogeissus latifolia*, *Asmunda japonica*, *Azadirachta indica*, *Butea frondosa*, *Butea monosperma*, *Cedrus deodara*, Chamomile, *Derris scandens*, *Portulaca oteracea*, *Eclipta prostrala*, *Emblica officinalis*, *Erythina indica*, *Ficus benghalensis*, *Glycyrrhiza glabra*, *Humilus scandens*, *Ilex purpurea Hassk*, *Inmula racemosa*, *Ixora chinensis*, *Ligusticum chiangxiong*, *Ligusticum lucidum*, *Mallotus philippinensis*, *Medemia noblis*, *Melicope hayesii*, *Mimusops elengi*, *Morinda citrifolia*, *Moringa oleifera*, *Naringi crenulata*, *Nerium indicum*, *Piper betel*, *Portulaca oteracea*, *Pouzolzia petandra*, *Psoratea corylifolia*, *Rhinacanthus nasutus*, *Sapindus rarek*, *Sesbania grandiflora*, *Stenoloma chusana*, *Terminalia bellerica*, *Tiliacora triandra*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol, thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

A sunscreen for protecting the skin from damaging ultraviolet rays may also be included. Preferred sunscreens are those with a broad range of UVB and UVA protection, such as octocrylene, avobenzone (Parsol 1789), octyl methoxycinnamate, octyl salicylate, oxybenzone, homosylate, benzophenone, camphor derivatives, zinc oxide, and titanium dioxide. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

In one embodiment, the composition of the invention comprising an N-heteroarylbisamide may have a pH between about 1 and about 8, In certain embodiments, the pH of the composition will be acidic, i.e., less than 7.0, and preferably will be between about 2 and about 7, more preferably between about 3.5 and about 5.5.

The invention provides a method for improving aging skin by topically applying a composition comprising a N-heteroarylbisamide, preferably in a cosmetically acceptable vehicle, over the affected area for a period of time sufficient to reduce, ameliorate, reverse or prevent dermatological signs of aging. This method is particularly useful for treating signs of skin photoaging and intrinsic aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; Increasing cell proliferation and/or multiplication; increasing skin cell metabolism decreased by aging and/or menopause; retarding cellular aging; improving skin moisturization; enhancing skin thickness; increasing skin elasticity and/or resiliency; enhancing exfoliation; improving microcirculation; decreasing and/or preventing cellulite formation, e.g., on the thighs; alleviating the appearance and formation of stretch marks; and any combinations thereof.

Without wishing to be bound by any particular theory, it is believed that the compositions of the present invention enhance and improve the aesthetic appearance of skin by stimulation of collagen and/or hyaluronic acid and restoring and maintaining homeostasis of these components.

The composition will typically be applied to the skin one, two, or three times daily for as long as is necessary to achieve desired anti-aging benefit. The treatment regimen may comprise daily application for at least one week, at least two weeks, at least four weeks, at least eight weeks, or at least twelve weeks. Chronic treatment regimens are also contemplated. In further embodiments, trans dermal patches including single-layer, multi-layer, reservoir, matrix patches and the like in the form of nose strips, peel-off paper masks, specialized treatment patches for eyes and facial contours, etc.; bandages including gauze, tube, and the like; poultices such as those used as facial masks, etc. are used to administer the cosmetic compositions of the current invention to areas of skin in need thereof for extended periods of time.

The N-heteroarylbisamide active component is topically applied to an "individual in need thereof," by which is meant an individual that stands to benefit from reducing visible signs of skin damage or aging. In a specific embodiment, the N-heteroarylbisamide component is provided in a physiologically, cosmetically, and dermatologically-acceptable vehicle, diluent, or carrier, where the composition is topically applied to an affected area of skin and left to remain on the affected area in an amount effective for improving the condition and aesthetic appearance of skin.

In one embodiment, methods for treating fine lines and wrinkles comprise topically applying the inventive N-heteroarylbisamide compositions to the skin of an individual in need thereof, e.g., topical application directly to the fine line and/or wrinkle in an amount and for a time sufficient to reduce the severity of the fine lines and/or wrinkles or to prevent or inhibit the formation of new fine lines and/or wrinkles. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). This embodiment includes treatment of wrinkles on the skin of the hands, arms, legs, neck, chest, and face, including the forehead.

It is also contemplated that the compositions of the invention will be useful for treating thin skin by topically applying the composition to thin skin of an individual in need thereof. "Thin skin" is intended to include skin that is thinned due to chronological aging, menopause, or photo-damage. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in subjects that have not manifested signs of skin aging, most commonly in individuals under 25 years of age. The method may also reverse or treat signs of aging once manifested as is common in subjects over 25 years of age.

The following example is meant to demonstrate certain aspects of the invention in a non-limiting fashion.

EXAMPLES

Example 1

Explant Assays

Samples of explanted skin tissue were obtained from an abdominal plasty of a 47 year old Caucasian woman. Samples (33 samples in total) were maintained in tissue culture medium at 37° C. in a humid, 5%-$CO_2$ atmosphere for the duration of the study.

The skin tissue explants were then distributed into appropriate controls or treated samples in triplicates. The controls received only a vehicle, and the treatment samples received 0.025 weight percent of Analog A disclosed above. The vehicle and Analog A were administered to the controls and treatment samples, respectively, on days 0, 1, 2, 5, and 7.

After nine days in culture the vehicle and Analog A treated samples were collected and processed for histology and immunostaining. Initially, the samples were fixed in buffered formalin for 24 hours. After which, the samples were dehydrated and impregnated in paraffin using a Leica TP 1020 Tissue Processor (Leica Microsystems, Wetzlar, Germany) in accordance with the vendor's protocol. Tissue sections were then made using a Leica RM 2125 Rotary microtome in accordance with the vendor laboratory protocol. The resulting sections were mounted on Superfrost® histological glass slides (Thermo Fisher Scientific, Waltham, Mass.), Slides were stained for hematoxylin and eosin stain according to standard protocol, Tissue samples were also stained for procollagen I using a Procollagen I rat monoclonal antibody with streptavidin alkaline phosphatase conjugate (Vectastain, Vector labs) and Vector® blue substrate detection system (Vector Laboratories LTD., Peterborough, UK), and hyaluronic acid using biotinylated affinity purified Hyaluronic Acid Binding Protein ((bovine nasal cartilage) Calbiochem, EMD Chemicals USA) and detected using the aforementioned detection system

Stained tissue sections (in triplicates) were examined for qualitative and semi-quantitative differences between treated and control samples at low and high power using Zeiss Mimax and Midi BF microscope and software system.

Figure 1A:
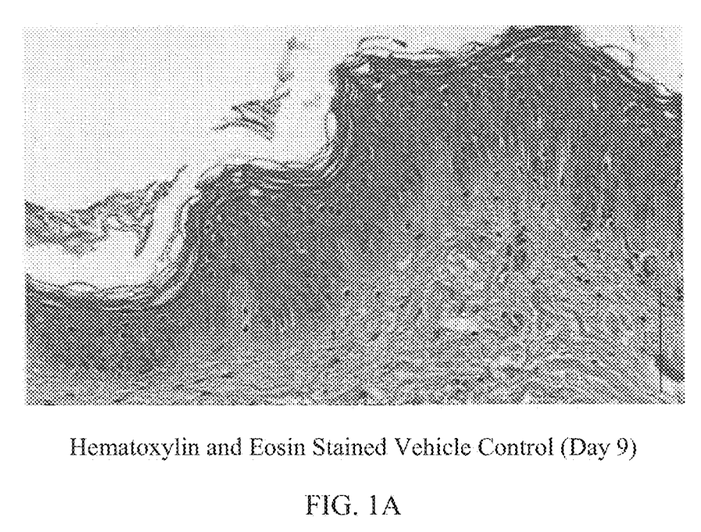
FIGS. 1A-B depict hematoxylin and eosin stained tissue explants for a comparison of the histology of explanted skin cells treated with a vehicle control (FIG. 1A) and Analog A (FIG. 1B) nine days after treatment was initiated.
Figure 1B:
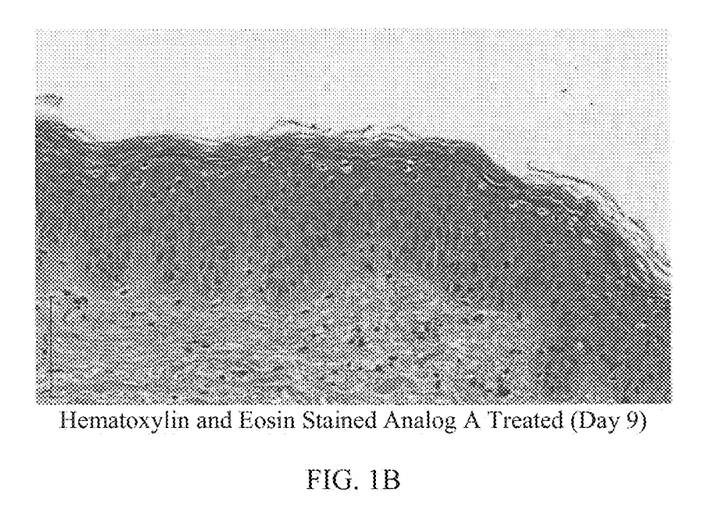
Figure 2A:
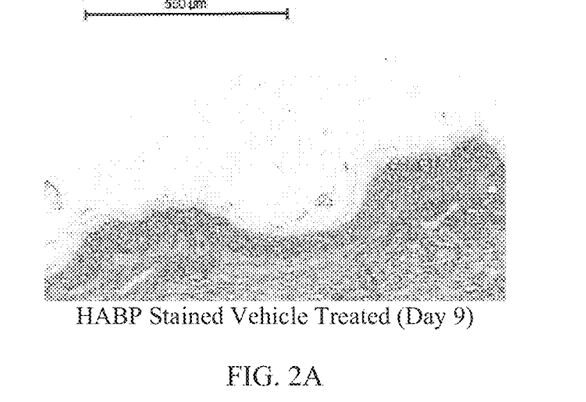
FIGS. 2A-B depict Hyaluronic Acid Binding Protein stained tissue explants to evaluating the presence of hyaluronic acid in explanted skin cells treated with a vehicle control (FIG. 2A) and Analog A (FIG. 2B) nine days after treatment was initiated.
Figure 2B:
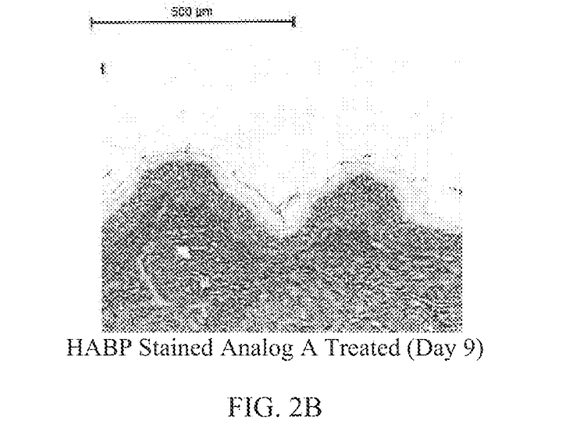
Figure 3A:
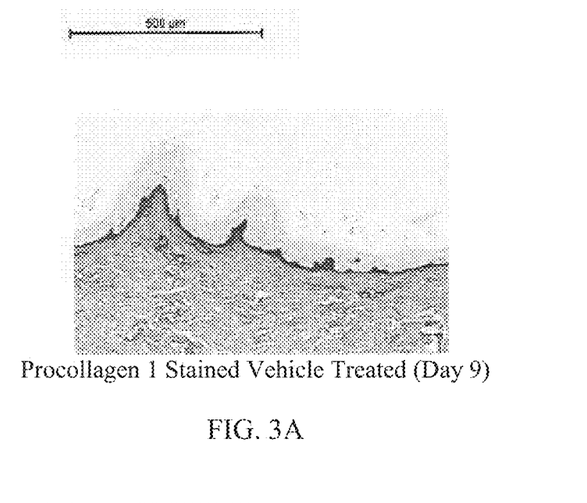
FIGS. 3A and B depict procollagen 1 immunostained explanted cells to evaluate the presence of the collagen precursor in vehicle control (FIG. 3A) and Analog A treated (FIG. 3B) explanted cells nine days after treatment was initiated.
Figure 3B:
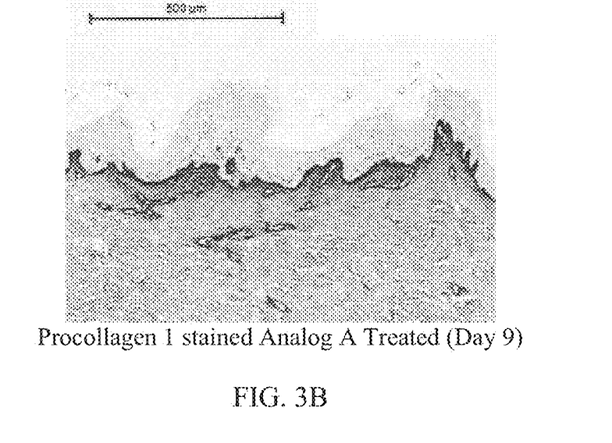

FIGS. 1A (vehicle control) and 1B (Analog A) depict representative results of the hematoxylin and eosin stain staining. The skin explains treated with Analog A (FIG. 1B) exhibited good contact with the basal layer and maintained their cell density throughout the basal epidermis.

Further Analog A increased the expression of Hyaluronic Acid and Procollagen 1 in comparison to the vehicle control as demonstrated by the comparison of FIGS. 2A and 2B and FIGS. 3A and 3B, respectively. This demonstrates that the N-heteroarylbisamide analog stimulates both procollagen/collagen and hyaluronic acid production, and potentially counteracts skin defects due to a decline in collagen and/or hyaluronic acid.

All references including patent applications and publications cited herein are incorporated herein by reference in their entirety and for all purpose to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:
1. A cosmetic composition for topical application to human skin comprising a cosmetically acceptable vehicle and a dermatologically effective amount of a N— heteroarylbisamide of Formula IA:

where:
$R_2$, $R_{2'}$, $R_6$, and $R_7$ are independently H, $C_1$-$C_8$ alkyl, heteroalkyl, alkoxyalkyl, heteroalkoxyalkyl, $C_3$-$C_8$ cycloalkyl, heterocycloalkyl, aryl, heteroaryl, alkyl-aryl, heteroalkyl-aryl, aryl-alkyl, and/or heteroaryl-alkyl;

$R_1$ and $R_5$ are independently H, $C_1$-$C_8$ alkyl, heteroalkyl, alkoxyalkyl, heteroalkoxyalkyl, $C_3$-$C_8$ cycloalkyl, heterocycloalkyl, aryl, heteroaryl, alkyl-aryl, heteroalkyl-aryl, aryl-alkyl, and/or heteroaryl-alkyl or WR wherein W is CO, $CO_2$, CONH, $SO_2$, $PO_3$, or $CH(Oalkyl)_2$; and n is 1-4.

2. The cosmetic composition of claim 1, wherein $R_7$ is H, halogen, or $C_1$-$C_4$ alkyl or alkoxy.

3. The cosmetic composition of claim 2, wherein $R_7$ is chlorine or methyl.

4. The cosmetic composition of claim 1, wherein $R_2$ is $C_1$-$C_6$ alkyl, or a $C_6$ aromatic hydrocarbon radical.

5. The cosmetic composition of claim 4, wherein $R_2$ is methyl or tert-butyl.

6. The cosmetic composition of claim 1, wherein $R_2$ is H or phenyl.

7. The cosmetic composition of claim 1, wherein $R_6$ is propyl, substituted propyl, or substituted phenyl.

8. The composition of claim 1, wherein $R_1$ and $R_5$ are independently H, or lower alkyl.

9. The composition of claim 1, wherein n is 3.

10. The cosmetic composition of claim 1, wherein said N-heteroarylbisamide has the structure:

11. A method for improving the aesthetic appearance of human skin comprising topically applying to an area of the skin in need thereof an amount of the cosmetic composition of claim 1 to enhance the skin.

12. The method according to claim 11, wherein the skin enhancement is an increase in the production of procollagen or collagen, and the aesthetic improvement is selected from the group consisting of:
(a) treatment and/or reduction of the appearance of fine lines or wrinkles,
(b) improvement of the skin's thickness, plumpness, and/or tautness;
(c) improvement in skin barrier repair and/or function;
(d) improvement in appearance of skin contours;
(e) increase in skin elasticity and/or resiliency;
(f) treatment and/or reduction of skin sagging;
(g) smooth scars and stretch marks; and/or
(h) reduction in pore size.

13. The method according to claim 11, wherein the skin enhancement is an increase in the production of hyaluronic acid and the aesthetic improvement is selected from the group consisting of:
(a) improvement in the skin's suppleness, softness, tone, radiance, and/or clarity;
(b) improvement in skin texture and/or promotion of retexturization;
(c) restoration of skin luster and/or brightness;
(d) replenishment of essential nutrients and/or constituents in the skin; and/or
(e) improvement of skin moisturization and/or complexion.

14. The method according to claim 11, wherein the skin enhancement is the modulation of fibroblasts and the aesthetic improvement is selected from the group consisting of:
(a) increase in the production of structural proteins and glucosaminoglycans;
(b) improvement in the structure of collagen;
(c) homoeostasis of structural protein and glucosaminoglycans;
(d) down-regulation of cytokine production;
(e) increased activation of fibroblasts to fibrocytes;
(f) increase in the viability and/or function of fibroblasts;
(g) improvement in maintenance and remodeling of elastin; and/or
(h) improvement in skin barrier repair and/or function.

15. The method according to claim 11, wherein the skin enhancement is the modulation of kertinocytes and the aesthetic improvement is selected from the group consisting of:
(a) improve the viability and/or function of the keratinocytes
(b) down-regulate the production of inflammatory factors and/or cytokines;
(c) improve skin barrier repair and/or function;
(d) improve thickness of the epidermis;
(e) improve uniformity of epidermal cells;
(f) improvement in pigmentation; and/or
(g) smooth scars and stretch marks.

16. The method of claim 11, wherein the skin enhancement is improving and maintaining the quality and viability of the extracellular matrix and the aesthetic improvements is selected from the group consisting of:
(a) treatment and/or reduction of the appearance of fine lines or wrinkles;
(b) improvement in the skin's thickness, plumpness, and/or tautness;
(c) improvement in skin barrier repair and/or function;
(d) improvement in appearance of skin contours;
(e) increased skin elasticity and/or resiliency;
(f) treatment and/or reduction of skin sagging;
(g) smoothing scars and stretch marks;
(h) reduction of pore size;
(i) improvement in the skin's suppleness, softness, tone, radiance, and/or clarity;
(j) improvement in the skin texture and/or promotion of its retexturization;
(k) restoration of skin luster and/or brightness;
(k) replenishment of essential nutrients and/or constituents in the skin; and/or
(l) improvement in skin moisturization and/or type.

17. The method according to claim 11, wherein the skin enhancement is improving and maintaining the quality and viability of the epidermis and the aesthetic improvement is selected from the group consisting of:
(a) improvement in skin barrier repair and/or function;
(b) improvement of thickness of the epidermis;
(c) improvement in uniformity of epidermal cells;
(d) improvement in pigmentation; and/or
(e) smoothing scars and stretch marks.

18. The method of claim 11 wherein the dermatologically effective amount of the cosmetic composition is applied to the area of skin in need thereof for a time sufficient to improve the area of skin's aesthetic appearance.

19. The method according to claim 18, wherein the composition is applied to said skin at least once daily for a period of at least four weeks.

20. The cosmetic composition of claim 1, further comprising from about 0.0001% to about 25% by weight of the N-heteroarylbisamide of Formula I.

21. The cosmetic composition according to claim 1, wherein said cosmetically acceptable vehicle comprises a water-in-oil or oil-in-water emulsion.

* * * * *